United States Patent
Weber

(10) Patent No.: US 7,491,304 B2
(45) Date of Patent: Feb. 17, 2009

(54) CARRIERLESS ELECTROPHORESIS PROCESS AND ELECTROPHORESIS DEVICE FOR CARRYING OUT THIS PROCESS

(75) Inventor: Gerhard Weber, Kirchheim (DE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 515 days.

(21) Appl. No.: 10/450,829

(22) PCT Filed: Dec. 7, 2001

(86) PCT No.: PCT/EP01/14408

§ 371 (c)(1), (2), (4) Date: Jun. 18, 2003

(87) PCT Pub. No.: WO02/50524

PCT Pub. Date: Jun. 27, 2002

(65) Prior Publication Data

US 2004/0045826 A1 Mar. 11, 2004

(30) Foreign Application Priority Data

Dec. 18, 2000 (DE) ............................... 100 63 097

(51) Int. Cl.
*G01N 27/447* (2006.01)
(52) U.S. Cl. ...................................... 204/450; 204/600
(58) Field of Classification Search ......... 204/450–455, 204/549, 600–606, 645, 548, 550, 644
See application file for complete search history.

(56) References Cited

U.S. PATENT DOCUMENTS

| | | | |
|---|---|---|---|
| 2,555,487 A | | 6/1951 | Haugaard et al. |
| 2,708,658 A | * | 5/1955 | Rosanberg ................. 204/630 |
| 2,878,178 A | | 3/1959 | Bier |
| 3,085,956 A | | 4/1963 | Caplan |
| 3,125,500 A | | 3/1964 | Grassman et al. |

(Continued)

FOREIGN PATENT DOCUMENTS

DE 42 32 781 C 10/1993

(Continued)

OTHER PUBLICATIONS

P. Todd, K.S.M.S. Rghavarao, S. Sengupta, J.F. Doyle, J. Vellinger, M.S. Deuser, "Multistage electrophoresis system for the separation of cells, particles and solutes", Electrophoresis, 21 (Jan. 24, 2000) 318-324.*
Computerized English translation of JP 06-130035.*

*Primary Examiner*—Alex Noguerola
(74) *Attorney, Agent, or Firm*—Mark Lindsey

(57) ABSTRACT

A free flow electrophoresis method for separating sample substances into their analytes. This method comprises multiple steps: a first step for the crude fractionation of the sample substance and at least one second step in which the crudely fractionated sample substance is finely fractionated. These steps can be performed in a parallel simultaneous method, in a serial method or in a combination of these two methods.

8 Claims, 5 Drawing Sheets

3 SEPARATE MEDIA INLETS

3 SEPARATE SEPARATION SPACES

SEPARATE SEPARATION SPACE 1 FOR THE COARSE FRACTIONATION (FRACTIONATION SITES n1<15)

TRANSFER OF PARTS OF FRACTIONS FROM SEPARATION SPACE 1 TO SEPARATION SPACE 2
SEPARATE SEPARATION SPACE 2 WITH FRACTIONATION SITES (n2>15)
TRANSFER OF n2 FRACTIONS TO THE SEPARATE SPACE 3
SEPARATE SEPARATION SPACE 3 WITH FRACTIONATION SITES (n3>50)

MEDIA INLETS — FRACTIONATION OUTLETS — PARTIAL FLOW FOR NEXT STAGE

U.S. PATENT DOCUMENTS

| | | | |
|---|---|---|---|
| 3,140,714 A | 7/1964 | Murphy, Jr. et al. | |
| 3,149,060 A | 9/1964 | Dobry et al. | |
| 3,287,244 A | 11/1966 | Mel | |
| 3,320,148 A | 5/1967 | Skeggs | |
| 3,320,149 A | 5/1967 | Isreeli | |
| 3,412,007 A | 11/1968 | Strickler | |
| 3,412,008 A | 11/1968 | Strickler | |
| 3,458,427 A * | 7/1969 | Strickler | 204/645 |
| 3,458,428 A * | 7/1969 | Huebner | 204/600 |
| 3,498,905 A | 3/1970 | Strickler | |
| 3,509,035 A | 4/1970 | Huebner | |
| 3,519,549 A | 7/1970 | Grassmann | |
| 3,616,454 A * | 10/1971 | Levy et al. | 204/615 |
| 3,616,455 A | 10/1971 | Munchhausen | |
| 3,655,541 A | 4/1972 | Strickler | |
| 3,663,395 A | 5/1972 | Strickler | |
| 3,668,107 A | 6/1972 | Lappe | |
| 3,755,132 A | 8/1973 | Kolin et al. | |
| 3,758,395 A | 9/1973 | Strickler | |
| 3,821,102 A | 6/1974 | Fletcher et al. | |
| 3,847,773 A | 11/1974 | Snyder | |
| 3,989,613 A | 11/1976 | Gritzner | |
| 4,043,895 A | 8/1977 | Gritzner | |
| 4,061,560 A | 12/1977 | Hannig et al. | |
| 4,107,027 A | 8/1978 | Muckenmuller et al. | |
| 4,141,809 A | 2/1979 | Aitchison et al. | |
| 4,204,929 A | 5/1980 | Bier | |
| 4,214,981 A | 7/1980 | Giddings | |
| 4,310,408 A | 1/1982 | Rose et al. | |
| 4,358,358 A | 11/1982 | Rhodes | |
| 4,362,612 A | 12/1982 | Bier | |
| 4,383,905 A | 5/1983 | Richman | |
| 4,394,246 A | 7/1983 | Richman et al. | |
| 4,396,477 A * | 8/1983 | Jain | 204/530 |
| 4,440,638 A | 4/1984 | Judy et al. | |
| 4,465,582 A | 8/1984 | Richman | |
| 4,749,458 A | 6/1988 | Muroi et al. | |
| 4,874,507 A | 10/1989 | Whitlock | |
| 4,897,169 A | 1/1990 | Bier et al. | |
| 5,032,247 A | 7/1991 | Tarnopolsky | |
| 5,047,135 A * | 9/1991 | Nieman | 204/619 |
| 5,066,377 A * | 11/1991 | Rosenbaum et al. | 204/466 |
| 5,071,536 A * | 12/1991 | Ivory | 204/549 |
| 5,087,338 A | 2/1992 | Perry et al. | |
| 5,131,994 A | 7/1992 | Shmidt et al. | |
| 5,133,844 A | 7/1992 | Stevens | |
| 5,173,164 A * | 12/1992 | Egen et al. | 204/515 |
| 5,180,480 A * | 1/1993 | Manz | 204/644 |
| 5,277,774 A | 1/1994 | Shmidt et al. | |
| 5,336,387 A | 8/1994 | Egen et al. | |
| 5,439,571 A | 8/1995 | Sammons et al. | |
| 5,447,612 A | 9/1995 | Bier et al. | |
| 5,540,826 A | 7/1996 | Bier et al. | |
| 5,562,812 A | 10/1996 | Carlson et al. | |
| 5,882,495 A * | 3/1999 | Garrels | 204/456 |
| 5,906,724 A | 5/1999 | Sammons et al. | |
| 5,954,931 A * | 9/1999 | Maracas et al. | 204/451 |
| 5,972,190 A | 10/1999 | Richman | |
| 6,210,574 B1 | 4/2001 | Sammons et al. | |
| 6,328,868 B1 | 12/2001 | Weber | |
| 6,749,733 B1 | 6/2004 | Sibbett | |
| 6,758,953 B2 * | 7/2004 | Thomas et al. | 204/450 |
| 6,793,791 B2 | 9/2004 | Bier | |
| 2001/0040095 A1 | 11/2001 | Shimizu et al. | |
| 2001/0040096 A1 | 11/2001 | Yamamoto et al. | |
| 2002/0008027 A1 | 1/2002 | Rhodes et al. | |
| 2004/0031683 A1 | 2/2004 | Eipel et al. | |
| 2004/0045826 A1 | 3/2004 | Weber | |
| 2004/0050697 A1 | 3/2004 | Eckerskorn et al. | |
| 2004/0050698 A1 | 3/2004 | Eckerskorn et al. | |
| 2004/0163956 A1 | 8/2004 | Bier | |

FOREIGN PATENT DOCUMENTS

| | | |
|---|---|---|
| EP | 0 203 713 A | 12/1986 |
| EP | 0081375 B1 | 4/1989 |
| EP | 0 497 077 A | 8/1992 |
| JP | 061162741 A | 7/1986 |
| JP | 061215952 A | 9/1986 |
| JP | 061215953 A | 9/1986 |
| JP | 063067557 A | 3/1988 |
| JP | 063117252 A | 5/1988 |
| JP | 06-130035 * | 5/1994 |
| JP | 2001091497 A | 4/2001 |
| JP | 2001153841 A | 6/2001 |
| JP | 2003247980 A | 9/2003 |
| JP | 2004113079 A | 4/2004 |
| JP | 061095241 A | 1/2009 |
| WO | 9110129 | 7/1991 |
| WO | 04077039 | 9/2004 |

* cited by examiner

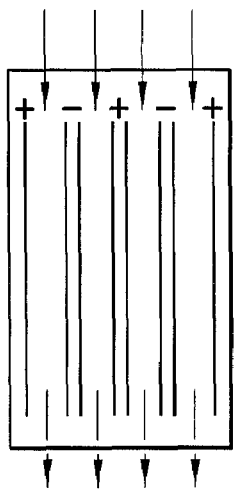

FIG. 1

4 SEPARATE MEDIA SUPPLIES

4 SEPARATE SEPARATION SPACES

4 SEPARATE FRACTIONATIONS WITH n FRACTIONATING SITES RESPECTIVELY
n<15

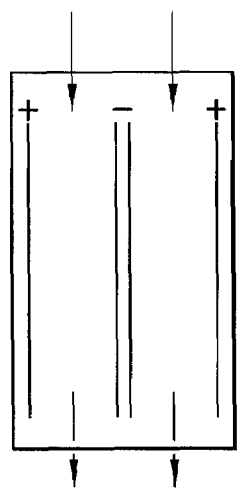

FIG. 2

2 SEPARATE MEDIA INLETS

2 SEPARATE SEPARATION SPACES

2 SEPARATE FRACTIONATIONS WITH n FRACTIONATING SITES RESPECTIVELY
n>50

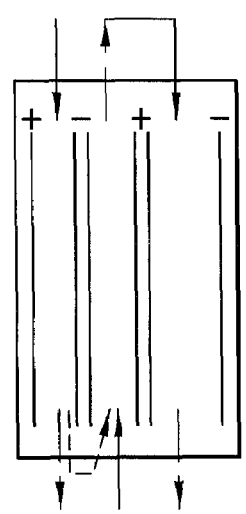

FIG. 3

3 SEPARATE MEDIA INLETS

3 SEPARATE SEPARATION SPACES

SEPARATE SEPARATION SPACE 1 FOR THE COARSE FRACTIONATION (FRACTIONATION SITES n1<15)

TRANSFER OF PARTS OF FRACTIONS FROM SEPARATION SPACE 1 TO SEPARATION SPACE 2

SEPARATE SEPARATION SPACE 2 WITH FRACTIONATION SITES (n2>15)

TRANSFER OF n2 FRACTIONS TO THE SEPARATE SPACE 3

SEPARATE SEPARATION SPACE 3 WITH FRACTIONATION SITES (n3>50)

→ MEDIA INLETS　　→ FRACTIONATION OUTLETS　　--→ PARTIAL FLOW FOR NEXT STAGE

CARRIERLESS ELECTROPHORESIS PROCESS AND ELECTROPHORESIS DEVICE FOR CARRYING OUT THIS PROCESS

This application is a 371 of PCT/EP01/14408, filed on Dec. 7, 2001, which claims priority from German application 10063097.9, filed on Dec. 18, 2000.

BACKGROUND OF THE INVENTION

1. Field of the Invention

The invention relates to a carrierless electrophoresis method for separating sample substances into their analytes and an electrophoresis device for carrying out this method.

2. Description of Related Art

Known carrierless FFE electrophoresis methods commonly operate with electrophoresis devices whose separation chamber is equipped with only two separate electrode spaces and only one separation space between these electrode spaces.

If, however, the FFE is to be used in the area of proteomics research, it must be possible to separate a large number of different sample substances within a short period, with a maximum separation output and with as high a rate of throughput of sample substances as possible.

However, as in the case of most separation processes, a simultaneous optimization of the electrophoresis device with regard to its separation performance and the sample throughput is difficult. In the case of FFE, simultaneous optimization is only possible within very narrow limits, as an increase in the quantity of the sample substance results in a reduction in the separation performance.

The optimization of the separation performance, moreover, requires a separation space with as narrow and precise a separation chamber gap as possible and specific separation boundary conditions, such as, e.g. a relatively low linear flow rate; as long a separation period as possible; and as many fractionation sites as possible over the entire width of the separation space and/or the area of the separation space in which the sample substance of interest is to be fractionated. However, since the linear flow rate cannot be reduced at will, an extension of the separation time requires a corresponding increase in the length of the electrodes. This in turn means that the outside dimensions of the separation chamber need to be increased simultaneously, making it difficult to manufacture the separation chamber gap with the desired accuracy.

Published German Patent Application DE 2 215 761 A1 discloses an electrophoresis device that operates according to an electrofiltration process. The electrophoresis device is equipped with a separation chamber, electrodes arranged on both sides of the separation chamber, fractionating sites and sample input sites, and several membranes in the separation chamber which divide the separation chamber into a large number of separation spaces connected to each other. The membranes serve as filters and are permeable to the species to be separated off in each case. Additionally, published European Patent Application EP 0 203 713 A2 discloses an electrophoresis device having a separate pair of electrodes for each of the separation spaces bounded by the membranes.

SUMMARY OF THE INVENTION

Consequently, an object on which the invention is based relates to creating a carrierless electrophoresis method and an electrophoresis device for carrying out this method, which allow for an increased separation performance, a shorter separation time and a greater throughput to be achieved.

An embodiment of the invention relates to a two-stage separation process that is used instead of a single stage separation process with simultaneous optimization of the separation performance and the sample throughput. This process effects a very rapid preliminary separation or coarse fractionation with the aim of achieving as high as possible a sample throughput and subsequently a targeted fine fractionation of the coarsely fractionated partial stream of the sample substance in at least a second stage.

An increase in the sample throughput in the first stage of coarse fractionation can be achieved by carrying out the separation process by means of FFE at an increased linear flow rate and with a simultaneously shortened migration path for the analytes to be separated. In this respect, the number of fractionation sites for coarse fractionation can be reduced considerably and a single fractionation site can be provided in the case that only one fraction is of interest. A further increase in the rate of sample throughput is possible if this two-stage process is carried out in the form of a parallel simultaneous multiple process.

In the following, preferred practical examples of the invention are described in further detail by way of the corresponding drawings.

BRIEF DESCRIPTION OF THE DRAWINGS

FIG. 1, FIG. 2 and FIG. 3 each show a diagrammatic view of the design of the separation chamber in the case of three embodiments of the invention.

DETAILED DESCRIPTION OF THE INVENTION

Figure 4:
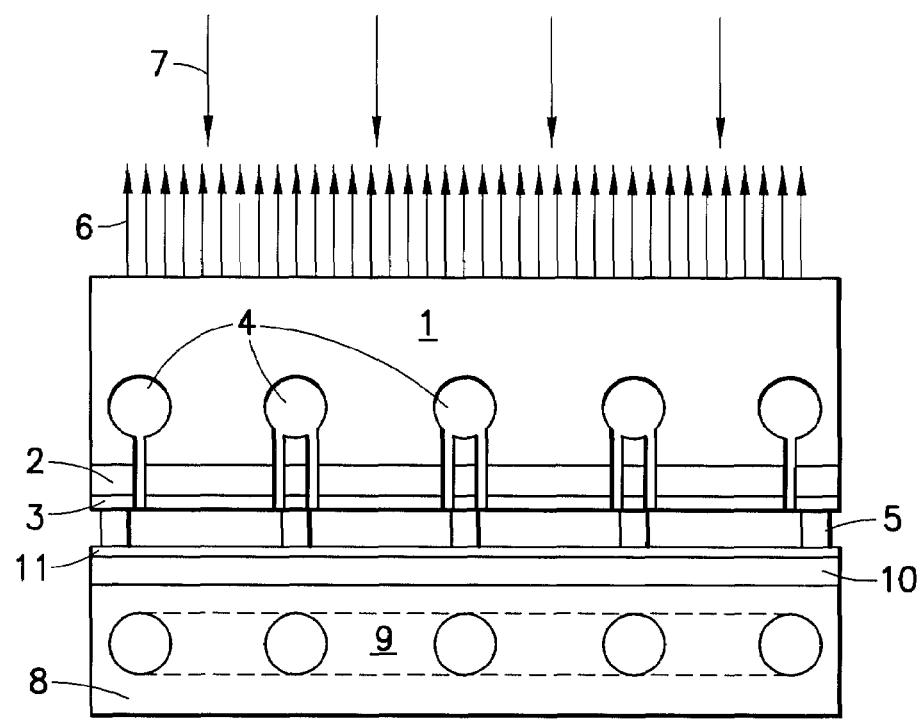
FIG. 4 and FIG. 5 each are a diagrammatic sectional view of the separation chamber in the case of an embodiment of the invention.

In FIGS. 1, 2 and 3, three examples of the separation chamber according to the invention are illustrated diagrammatically for different practical examples of the electrophoresis device. In order for the separation chamber to have an outside dimension which allows the separation chamber gap to be manufactured with sufficient accuracy, several separate separation spaces are provided in the separation chamber. According to FIG. 1, four separate separation spaces are provided with four separate media supplies for four separate fractionations with n fractionation sites, n being less than 15. FIG. 2 shows a separation chamber with two separate separation spaces and two separate media inlets for two separate fractionations with n fractionation sites, n being greater than 50. Finally, FIG. 3 shows a separation chamber with three separate separation spaces and three separate media inlets for two separate fractionations with n1 and n3 fractionation sites, n1 being less than 15 and n3 more than 50, and a further separate fractionation with n2 fractionation sites, n2 being greater than 15.

Depending on the design, the separation spaces illustrated in FIGS. 1 to 3 are equipped with separate electrodes or electrodes common with the adjacent separation spaces if identical media can be used in the electrode spaces concerned.

By means of the separation chambers illustrated in FIGS. 1 to 3, a carrierless FFE electrophoresis can be carried out for separating sample substances into their analytes in the form of an at least two-stage process, a coarse fractionation of the sample substance taking place in the first stage and a fine fractionation of the coarsely fractionated sample substance taking place in at least one second stage.

This process can be carried out as a parallel simultaneous operation or in a series operation, it being possible to use the separation spaces illustrated in FIGS. 1 and 2 in a parallel simultaneous operation as separation space for coarse fractionation (FIG. 1) and as a separation space for fine fractionation (FIG. 2). FIG. 3 shows the separation space for series operation in the form of a three-stage process in which coarse fractionation in series is combined with a two-stage fine fractionation.

In the case of the parallel method of operation, either a single sample substance can be metered simultaneously into several separation spaces or different sample substances can be applied to the separate separation spaces. The separation of the sample substances in the parallel simultaneous process makes it possible to increase the rate of throughput of the sample substances or increase the number of sample substances.

By reducing the width of the separate separation spaces, the migration path of the analytes can be shortened and the separation processes can be carried out at higher flow rates for the separation media and the sample substances. With an increasing number of separation spaces, the width of the separation spaces becomes substantially smaller with the consequence, however, that only one coarse fractionation is possible, albeit with a much higher sample throughput.

If the separation spaces are connected in series with completely separate electrode spaces, the fractions obtained by separation in one separation space are further fractionated in the subsequent separation spaces. The subsequent separation occurs under identical separation conditions, making it possible to achieve a higher separation output. When the separation spaces are connected in series, separation operations can also be carried out under different conditions depending on the separation techniques, the separation media and/or the general electrophoretic separation parameters used.

The separation spaces and the technical design of the individual separation spaces can be combined almost at will by means of the structure described above, as described in the following.

Figure 5:
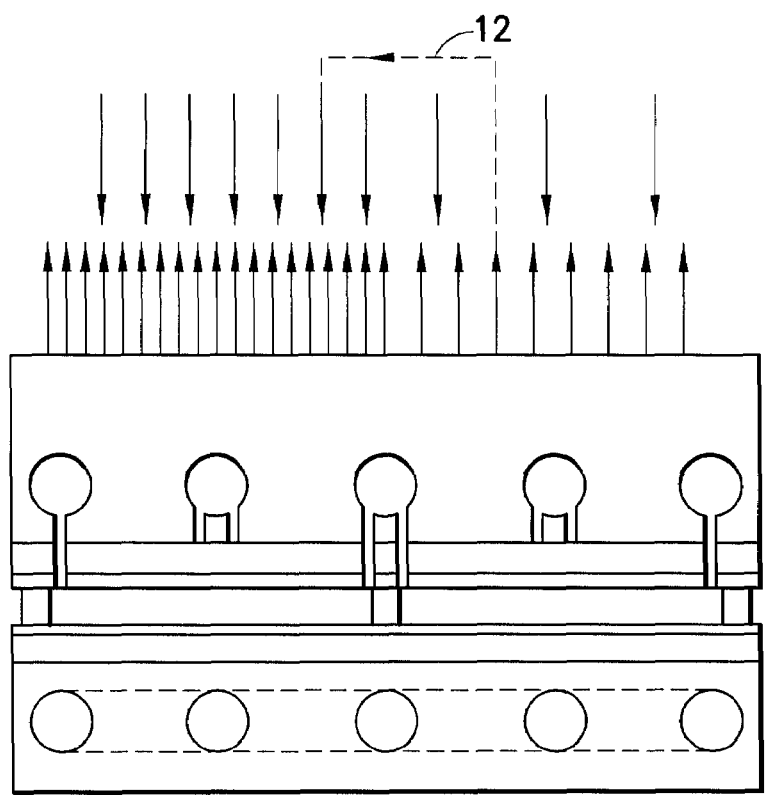

As illustrated in FIGS. 4 and 5, a separation chamber typically contains two sub-assemblies, namely the front part of the separation chamber and the rear part of the separation chamber. Preferably, the individual sub-assemblies contain several separate structural elements which are illustrated diagrammatically in FIG. 4 and FIG. 5.

FIG. 4, illustrates a separation chamber front part containing a synthetic resin block 1 with a rigid synthetic resin sheet 2, a flexible synthetic resin sheet 3, a separation chamber rear part containing a metal block 8 with a glass sheet 10 and a flexible synthetic resin sheet 11, which are arranged next to each other via spacers 5. In the synthetic resin block 1, several—five in the illustrated practical example—electrode spaces 4 are provided. In the metal block 8, there are cooling pipes 9. In addition, media inlets 7 and a large number of fractionation sites 6 are provided. FIG. 5 shows the transfer 12 of the pre-fractionated sample.

The sub-assembly of the front part of the separation chamber in FIG. 4 consequently consists of a basic building block, namely a solid block of PLEXIGLAS® 1 in which up to eight electrode spaces 4 and the openings for specific method modules of the media feeders and the fractionations are housed. To this basic building block 1, a thin sheet 2 of rigid synthetic resin material is applied, the latter exhibiting apertures for conveying the flow in the area of the electrode spaces of the synthetic resin block 1. The electrode spaces should not close the electrode spaces of the synthetic resin block 1. The same applies to the design of the rigid synthetic resin sheet 2 in the area of the media feeders 7 and the fractionations 6. The surface of the rigid synthetic resin sheet 2 facing the separation space can be either directly chemically modified or, in the manner illustrated, covered by a synthetic resin sheet 3 whose surface forms the direct boundary of the separation space. The surface may be chemically modified to minimize the effects of electro-osmosis and sorption of the sample species.

By way of the combination, as described, of the basic building block, i.e. the synthetic resin block 1, with the two synthetic resin sheets 2, 3 which are modified to suit specific applications, all the requirements described above regarding the number of separation stages, the geometry of the separation space and the special electrophoretic boundary conditions can be fulfilled in the stage of the separation process concerned.

Figure 6:
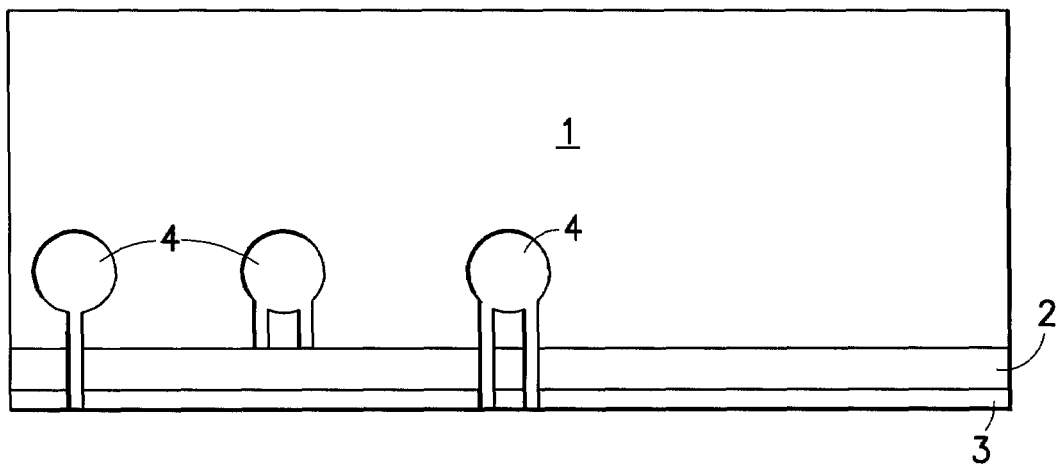
FIG. 6 and FIG. 7 show the structure of the front part of the separation chamber and the rear part of the separation chamber in the area of the media supplies and a fractionation, respectively.
Figure 7:
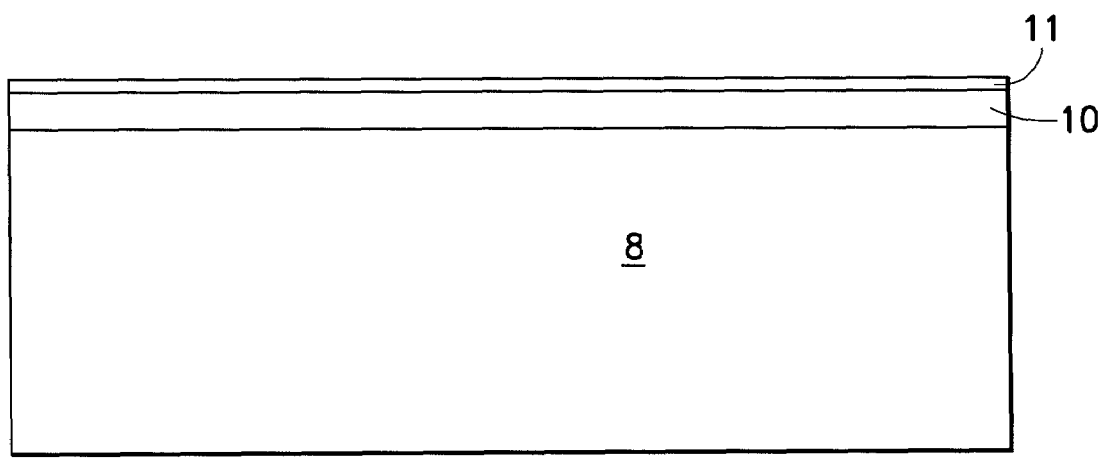

In FIGS. 6 and 7, the structure of the front part of the separation chamber and the rear part of the separation chamber are illustrated in detail. As shown in FIG. 7, the rear part of the separation chamber consists of several layers, namely the metal block 8, the glass sheet 10 and the flexible synthetic resin sheet 11. These layers can be combined in different ways in order to optimize the separation device for the application concerned.

The basic building block of the rear part of the separation chamber is consequently a solid metal block 8 which, in combination with an external cooling, allows the effective removal of the heat developed during electrophoretic separation. The surface of the metal block 8 facing the separation space is covered by an electrically insulating thin sheet 10 of glass or a ceramic sheet. This electrically insulating sheet may be covered by the synthetic resin sheet 11 whose surface, which forms the boundary of the separation space directly, may be chemically modified such that an optimization of the separation process is achieved. As a general rule, the synthetic resin sheets facing the separation space, i.e. sheets 3 and 11, can be identical or similar with respect to their material and the type of chemical modification; however, they can also be different in the case of certain process combinations.

Figure 8:
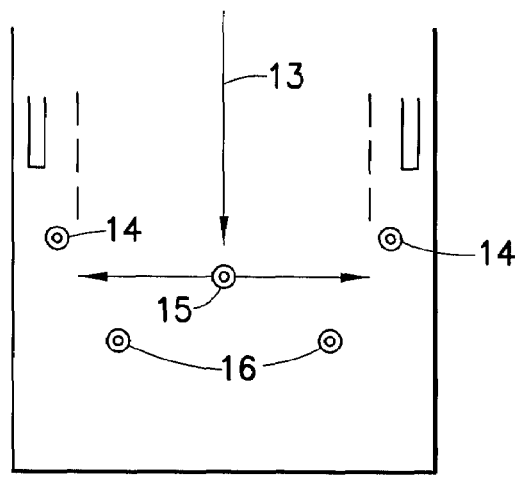
FIG. 8, FIG. 9 and FIG. 10 each show a relative spatial arrangement of the different fractionation sites and the cross-flow feeder lines.
Figure 9:
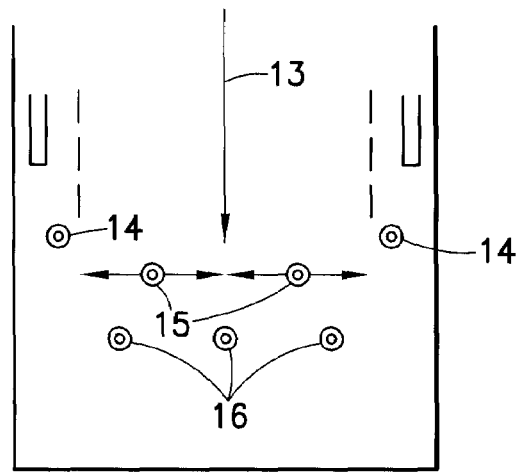
Figure 10:
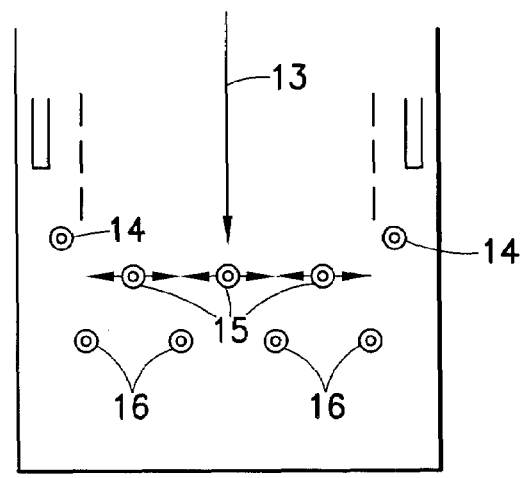

In FIGS. 8, 9 and 10, different fractionation modules are illustrated, which can be used for the method according to the invention. In its standard design, the fractionation module in FIG. 8 contains three outlets for fractionation. The module may also contain five to seven fractionation outlets in the case of special applications, as shown in FIG. 9 and FIG. 10 respectively. In these figures, the direction of flow of the separation medium is indicated by an arrow 13. The supply sites 14 for the cross-flow, the n fractionation sites 15 for the sample substance and n+1 outlets 16 for the remaining medium are also illustrated.

Figure 12:
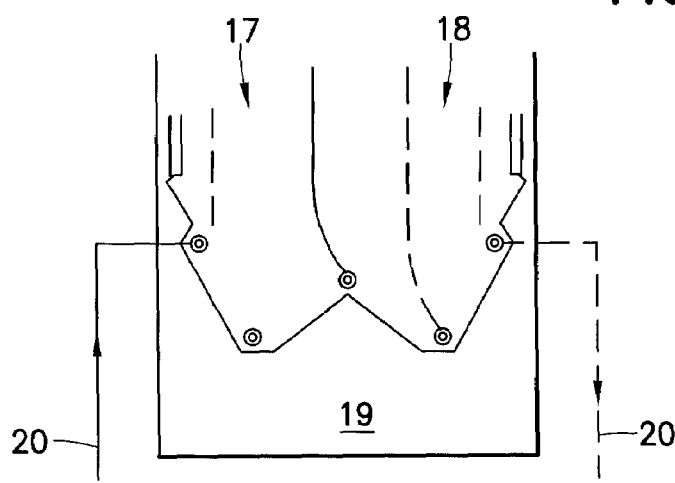
Figure 13:
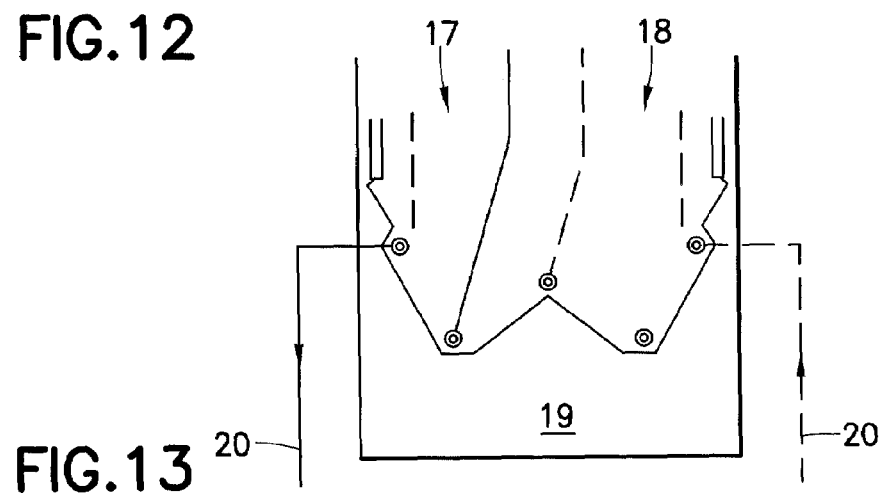

During operation, two separate conveyor channels with identical conveying rates of a metering pump are connected with the separation space in the area of the near-electrode fractionation outlets. A medium is introduced via a connection to the near-electrode separation space, depending on the sense of rotation of the conveyor pump, and, simultaneously, a medium is discharged from the separation space at the same volume rate, via a second connection. As a result of the simultaneous introduction and discharge of the medium in the near-electrode separation space, the flow profile is altered in the area of the fractionation site of the sample, as illustrated in FIGS. 11, 12 and 13.

Figure 11:
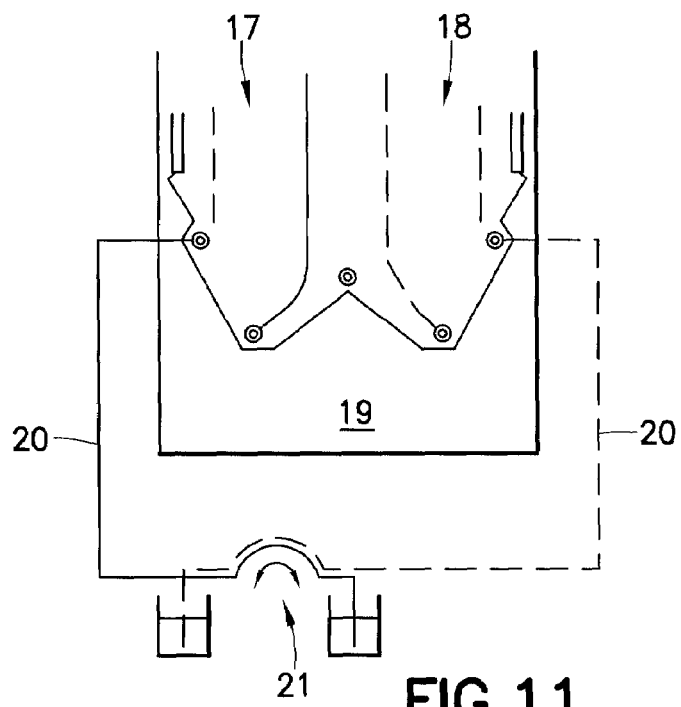
FIGS. 11, 12 and 13 each show the influencing of the flow profile by means of the cross-flow.

FIG. 11 shows two analytes 17, 18, a pump 21 for the cross-flow, the feeder line 20 for the cross-flow and the mask 19 for the flow profile. In FIG. 11, a flow profile without cross-flow is illustrated. FIG. 12 shows the profile with the cross-flow having been started up and FIG. 13 shows the flow profile with the cross-flow started up but with the opposite direction of rotation to the pump 21.

In the following, a preparative long-term test, i.e., the operation of the fraction module for two typical alternative applications is described:

During preparative isolation of any desired separated substance, the conveying rate of the two-channel pump is selected such that the substance to be isolated can be collected via the sample outlets provided for this purpose. The rate of conveying of the two-channel pump remains unchanged throughout the duration of preparative isolation. If the analyte being discharged in the sample fractionation line can be detected quantitatively with only a slight time delay, the detection signal for controlling the separation process can be used such that the analyte can be isolated with an optimum yield and purity.

If, however, the conveying rate of the pump is altered continuously during the electrophoretic separation process, substances separated one after the other are collected via the sample fractionation site. By changing the rate of conveying and by changing the sense of rotation of the two-channel pump, all species separated can be eluted in succession via the fractionation site and subsequently passed to a detection system and a fraction collector with a time-controlled or peak-controlled change-over of the collection vessels.

If a local displacement of the sample bands by more than 20 mm is to be achieved in the direction of the sample fractionation site, it is to be recommended to increase the number of sample fractionation outlets, it being possible to increase this number at will with higher values of the separation space width in order to permit an optimum elution quality of the samples.

The invention claimed is:

1. A carrierless electrophoresis method, comprising the steps of:
   (a) carrying out a coarse fractionation of a sample substance by carrierless electrophoresis in a first separation space as a first stage;
   (b) carrying out a fine fractionation of a targeted portion of the coarsely fractionated sample substances by carrierless electrophoresis in a second separation space as a second stage, wherein a smaller number of fractionation sites are used in step (a) than in step (b) wherein the first and second separation spaces are adjacent to one another and comprise at least one electrode positioned between the first and second separation spaces; and
   (c) optionally repeating step (b) one or more times.

2. The method according to claim 1, wherein step (a) comprises using a high linear flow rate and a short migration path to separate the sample substance.

3. The method according to claim 1, wherein step (a) and step (b) are carried out in parallel simultaneously.

4. The method according to claim 1, wherein the execution of one or more steps in a parallel simultaneous process is combined with a series execution of at least one other step.

5. The method according to claim 1, wherein step (a) and step (b) are carried out with identical media in each separation space.

6. An electrophoresis method, comprising the steps of:
   (a) carrying out a coarse fractionation of a sample substance by carrierless electrophoresis in a first separation space as a first stage;
   (b) carrying out a fine fractionation of a targeted portion of the coarsely fractionated sample substances by carrierless electrophoresis in a second separation space different than the first separation space as a second stage, wherein a smaller number of fractionation sites are used in step (a) than in step (b) wherein each of the first and second separation spaces are positioned between a common pair of sheets; and
   (c) optionally repeating step (b) one or more times.

7. The method of claim 6, wherein each of the pair of sheets are chosen from a material consisting of glass, ceramic and synthetic resin.

8. The method of claim 6, wherein the first and second separation spaces comprise identical media.

* * * * *